United States Patent
Wang et al.

(10) Patent No.: US 7,722,749 B2
(45) Date of Patent: May 25, 2010

(54) GAS SENSOR AND METHOD FOR FORMING SAME

(75) Inventors: Da Yu Wang, Troy, MI (US); Walter Thomas Symons, Grand Blanc, MI (US); Robert Jerome Farhat, Grosse Pte Park, MI (US); Sheng Yao, Macomb, MI (US); Joachim Kupe, Davisburg, MI (US)

(73) Assignee: Delphi Technologies, Inc., Troy, MI (US)

( * ) Notice: Subject to any disclaimer, the term of this patent is extended or adjusted under 35 U.S.C. 154(b) by 995 days.

(21) Appl. No.: 11/218,152

(22) Filed: Sep. 1, 2005

(65) Prior Publication Data

US 2007/0045114 A1 Mar. 1, 2007

(51) Int. Cl.
*G01N 27/407* (2006.01)
(52) U.S. Cl. .............. 204/426; 204/424; 205/780.5
(58) Field of Classification Search .......... 205/781, 205/783.5, 780.5; 204/421–429
See application file for complete search history.

(56) References Cited

U.S. PATENT DOCUMENTS

| | | | |
|---|---|---|---|
| 5,369,956 A | 12/1994 | Daudel et al. | |
| 6,532,736 B2 | 3/2003 | Hammerle et al. | |
| 2003/0116448 A1 | 6/2003 | Nakae et al. | |
| 2004/0118703 A1 | 6/2004 | Wang et al. | |

FOREIGN PATENT DOCUMENTS

| | | |
|---|---|---|
| DE | 199 01 956 | 8/2000 |
| JP | 03142353 | 6/1991 |

OTHER PUBLICATIONS

European Search Report dated Dec. 12, 2006.

*Primary Examiner*—Kaj K Olsen
*Assistant Examiner*—Kourtney R Salzman
(74) *Attorney, Agent, or Firm*—Thomas N. Twomey

(57) ABSTRACT

A sensor including a species selective electrode and a reference electrode having an electrolyte layer disposed therebetween; a reference gas channel in fluid communication with the reference electrode; a heater and a temperature sensor; wherein the species selective electrode is disposed on a first side of an insulating layer separating the species selective electrode from the electrolyte layer, the insulating layer having a first substantially solid area and a second area having an opening pattern extending through the insulating layer; the species selective electrode comprising a species sensing electrode portion disposed on the opening pattern of the insulating layer so as to contact the electrolyte layer through the opening pattern and a non-active electrode lead portion disposed over the first substantially solid area so that the non-active electrode lead portion is in electrical communication with the species sensing electrode portion and is free from contact with the electrolyte layer.

27 Claims, 7 Drawing Sheets

GAS SENSOR AND METHOD FOR FORMING SAME

TECHNICAL FIELD

The present disclosure relates to sensors and more particularly relates to exhaust gas species sensors and methods for forming same.

BACKGROUND

Exhaust gas sensors are used in a variety of applications that require qualitative and quantitative analysis of gases. For example, exhaust sensors have been used for many years in automobiles to sense the presence of selected exhaust gases. In automotive applications, the direct relationship between various exhaust gas concentrations and the air-to-fuel ratios of the fuel mixture supplied to the engine allows the sensor or sensors to provide concentration measurements for determination of optimum combustion conditions, maximization of fuel economy, and management of exhaust emissions.

For example, U.S. Pat. No. 6,616,820 to Wang et al. describes in the Abstract a gas sensor for sensing NOx (nitrogen oxides) having electrochemical cells wherein dielectric material surrounds electrolytes except where electrodes are attached. With the use of this technique, signal cross talk is minimized while enhancing NOx sensing sensitivity. Further, the total number of electrodes needed are reduced which allows for more complex sensor structures.

U.S. Pat. No. 6,797,138 to Detwiler et al. describes in the Abstract a gas sensor comprising a first electrode and a reference electrode with an electrolyte disposed therebetween, wherein the first electrode and the reference electrode are in ionic communication, wherein the reference electrode has a surface on a side of the reference electrode opposite the electrolyte and the surface has a surface area. The gas sensor also comprises a reference gas channel in fluid communication with the reference electrode, wherein at least a portion of the surface of the reference electrode physically contacts at least a portion of the reference gas channel, and wherein the portion of the reference electrode in physical contact with the reference gas channel is less than about 90% of the surface area.

U.S. Pat. No. 6,579,435 to Wang et al. describes in the Abstract a gas sensor and a method of using a gas sensor. The gas sensor comprises an oxygen pump cell having at least one exterior pump electrode and at least one interior pump electrode disposed on opposite sides of a first solid electrolyte layer. An emf cell having first and second emf electrodes and first and second reference gas electrodes are disposed on opposite side of a second solid electrolyte layer. At least one insulating layer is in contact with the first and second emf electrodes. At least one via hole is disposed through the first solid electrolyte layer. At least one air channel is disposed through at least one insulating layer. An air vent is disposed in at least one insulating layer in contact with the first and second reference gas electrodes. A heater is disposed in thermal communication with the sensor. And at least five electrical leads are in electrical communication with the sensor.

Particular to NOx sensors, treatment of the exhaust gas is employed prior to being analyzed using, for example, the Nernst and/or polarographic principles. Typically, this is achieved using catalyst and/or by maintaining the other gases at constant levels within an enclosed or semi-enclosed environment. Once the exhaust gas is treated, the gas encounters the sensor's electrochemical cells.

In order to meet some emission regulations, selective catalytic reduction systems using externally added reducing agents may be used. In such systems, regulated emissions, such as certain nitrogen oxides, or NOx, can be reduced in an oxygen-rich environment to nitrogen and water over a catalyst when a reducing agent, such as ammonia, is added. In addition to controlling nitrogen oxide emissions, the amount of excess ammonia, or ammonia slip, must be managed. Ammonia slip is experienced when ammonia in excess of that used to reduce the nitrogen oxides passes through the catalyst unaffected and exits the catalyst (as ammonia slip).

One method for regulating ammonia slip is to use an ammonia sensor located downstream of the catalyst. The detected ammonia concentration is compared with a fixed upper threshold value. This comparison generates a correction signal that is used to control the metering of ammonia upstream of the catalyst. In this scheme, it is believed that by regulating actual ammonia slip to the upper threshold value, a certain nitrogen oxide reduction is obtained. Such a system is disclosed in U.S. Pat. No. 5,369,956. Reference also U.S. Pat. Nos. 6,295,809 and 6,532,736.

The disclosures of each of the foregoing U.S. Patents are each incorporated herein by reference in their entireties. The appropriate components and process aspects of the each of the foregoing U.S. Patents may be selected for the present disclosure in embodiments thereof.

There remains a need for an improved exhaust gas species sensor and an improved method for preparing such a sensor. There further remains a need for a durable and fast response ammonia sensor and a method for preparing the same. Particularly, there is a need for an ammonia sensor that is stable at high temperature and high humidity environments, such as diesel engine exhaust applications, which is able to withstand exposure to diesel exhaust impurities (e.g., soot) with little or no degradation.

SUMMARY

Aspects illustrated herein relate to a sensor comprising a species selective electrode and a reference electrode having an electrolyte layer disposed therebetween; a reference gas channel in fluid communication with the reference electrode; a heater disposed in thermal communication with the sensor; a temperature sensor disposed in communication with the heater for maintaining the sensor at a desired operating temperature; wherein the species selective electrode is disposed on a first side of an insulating layer separating the species selective electrode from the electrolyte, the insulating layer having a first substantially solid area and a second area having an opening pattern extending through the insulating layer; the species selective electrode comprising a species sensing electrode portion comprising a first material disposed on the opening pattern of the insulating layer so as to contact the electrolyte layer through the opening pattern and a non-active electrode lead portion comprising a second material that is different from the first material disposed over the first substantially solid area so that the non-active electrode lead portion is in electrical communication with the species sensing electrode portion and is free from contact with the electrolyte layer; and wherein both the species selective electrode and the reference electrode are in fluid communication with an exhaust atmosphere.

Further aspects illustrated herein relate to a method for forming a sensor comprising disposing a species selective electrode and a reference electrode on opposite sides of an electrolyte layer; forming a reference gas channel in fluid communication with the reference electrode; disposing a heater in thermal communication with the sensor; disposing a temperature sensor in communication with the heater for maintaining the sensor at a desired operating temperature; disposing the species selective electrode on a first side of an insulating layer so as to separate the species selective electrode from the electrolyte layer, the insulating layer having a first substantially solid area and a second area having an opening pattern extending through the insulating layer; the species selective electrode comprising a species sensing electrode portion comprising a first material disposed on the opening pattern of the insulating layer so as to contact the electrolyte layer through the opening pattern and a non-active electrode lead portion comprising a second material that is different from the first material disposed over the first substantially solid area depositing the first material deposited on top of the second material so that the non-active electrode lead portion is in electrical communication with the species sensing electrode portion and is free of contact with the electrolyte layer, to form a green sensor; and firing or co-firing the green sensor.

Further aspects illustrated herein relate to an exhaust gas treatment system comprising a sensor comprising a species selective electrode and a reference electrode having an electrolyte layer disposed therebetween; a reference gas channel in fluid communication with the reference electrode; a heater disposed in thermal communication with the sensor; a temperature sensor disposed in communication with the heater for maintaining the sensor at a desired operating temperature; wherein the species selective electrode is disposed on a first side of an insulating layer separating the species selective electrode from the electrolyte layer, the insulating layer having a first substantially solid area and a second area having an opening pattern extending through the insulating layer; the species selective electrode comprising a species sensing electrode portion comprising a first material disposed on the opening pattern of the insulating layer so as to contact the electrolyte layer through the opening pattern and a non-active electrode lead portion comprising a second material that is different from the first material disposed over the first substantially solid area, the first material being deposited on top of the second material, so that the non-active electrode lead portion is in electrical communication with the species sensing electrode portion and is free from contact with the electrolyte layer; the species selective sensing element being disposed downstream of an exhaust catalyst for sensing a concentration of reductant in a catalyst treated exhaust gas; a controller in communication the species selective sensing element, an engine, and a reductant supply, for controlling the amount of reductant delivered to the exhaust gas exiting the catalyst.

These and other features and advantages of the invention will be more fully understood from the following description of certain specific embodiments of the invention taken together with the accompanying drawings wherein like elements are numbered alike in the figures.

DESCRIPTION

The species selective sensors described herein can be used in any exhaust treatment application, and are particularly useful in embodiments comprising ammonia ($NH_3$) sensors having a potential to measure the $NH_3$ content of diesel engine exhaust gas after a Selective Catalyst Reactor (SCR), for example, a urea Selective Catalyst Reactor (SCR) unit when mounted downstream of the SCR. The downstream value of $NH_3$ is determined and the measured value of $NH_3$ is stored for the engine electronic control unit (ECU) for determining a $NH_3$ dosage sufficient for neutralizing $NH_3$ present in diesel exhaust (de-NOx system). When the $NH_3$ is known, the de-NOx SCR system can be operated at its maximum efficiency and have its lifetime use maximized. For this application, the use of a NOx sensor is not beneficial since it cannot detect the $NH_3$ slip and further the presence of $NH_3$ would interfere with the NOx sensor.

Figure 1:
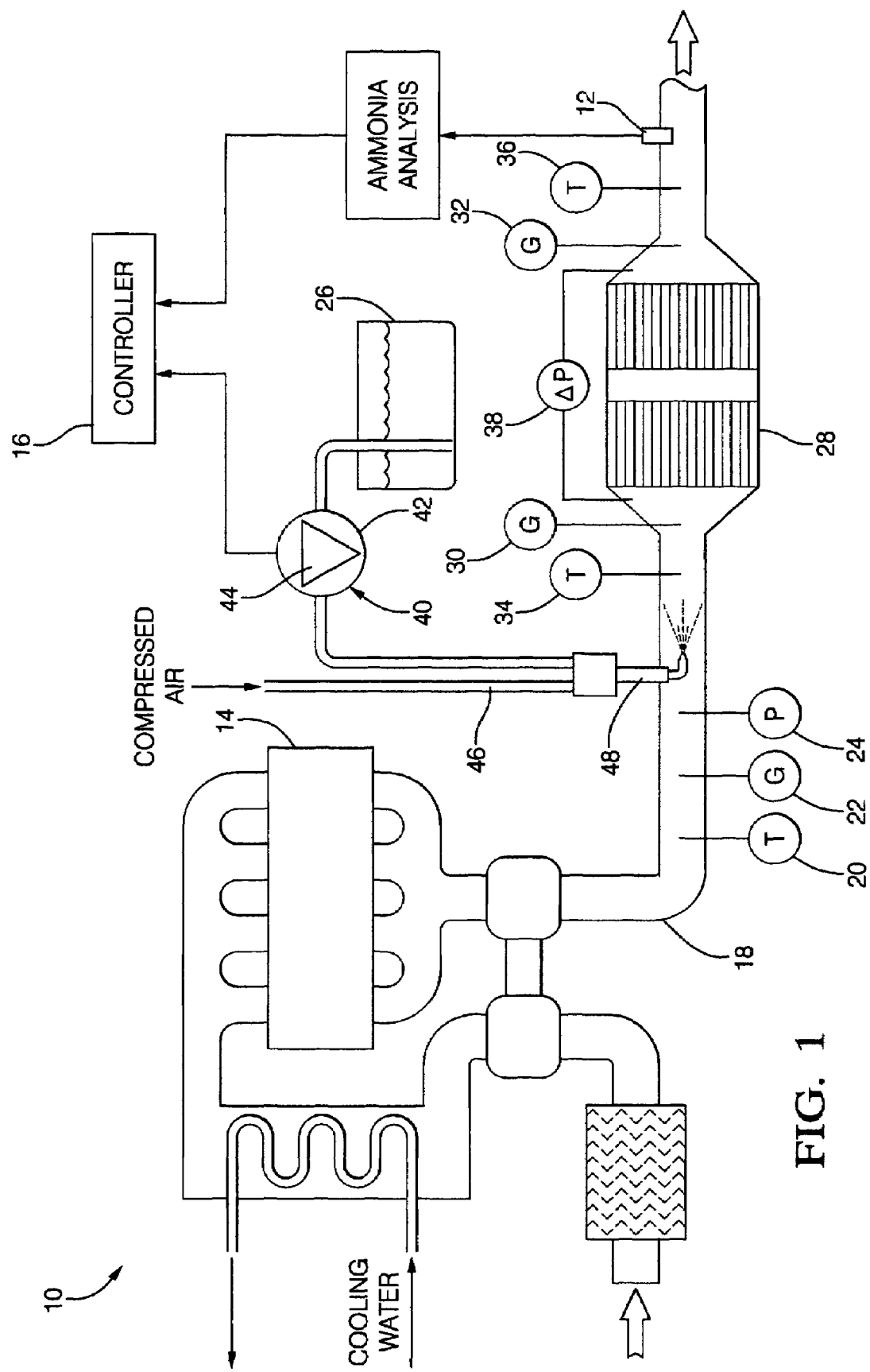
FIG. 1 is a schematic diagram of an ammonia sensor employed in a diesel exhaust after treatment urea-selective catalytic reduction system.

Referring now to FIG. 1, an $NH_3$ nitrogen oxides treatment system 10 (de-NOx system) employing a sensing element 12 including a species selective sensor (e.g., $NH_3$ sensor) for diesel engine 14 exhaust aftertreament is shown. While the discussion herein focuses on employing an ammonia sensor in a urea selective SCR system for treating diesel engine exhaust, the sensor may be any species selective sensor and the sensor(s) may be advantageously employed in numerous other system configurations and with other types of engines including, but not limited to, internal combustion engines, gas turbines, spark ignited engines, compression ignited engines, direct injection engines, etc. In FIG. 1, diesel engine 14 is controlled by electronic control unit (controller/ECU) 16. Engine 14 includes numerous known components not shown or partially illustrated including a combustion chamber and cylinders with pistons contained therein and connected to a crankshaft. Typically, the combustion chamber communicates with an intake manifold and an exhaust manifold 18 via various sensors including exhaust temperature sensor 20, exhaust gas sampling sensor 22, and exhaust pressure sensor 24 via valves (not shown). A fuel delivery system (not shown) such as a fuel injector is coupled to the intake manifold for delivering liquid fuel in proportion to the pulse width of a signal (FPW) from the controller 16. Fuel quantity, controlled by a signal FPW and injection timing is adjusted accordingly. Fuel is delivered to the fuel injector such as by a conventional fuel system (not shown) including a fuel tank, fuel pump, and fuel rail. Alternatively, the engine 14 may be configured such that the fuel is injected directly into the cylinder of the engine (direct injection engine).

In the system 10, a reducing agent, for example, urea, is stored in storage vessel 26 coupled to exhaust manifold 18 upstream of a selective catalytic reactor (SCR) converter (catalyst) 28. The reductant supply can comprise any suitable reducing agent, including, but not limited to, for example, a nitrogen (N) containing substance, ammonia, or ammonia prepared from urea. In the embodiment shown in FIG. 1, urea is continuously replenished into the exhaust 18 together with water. The urea then reacts with water to form $NH_3$ and $CO_2$ through the hydrolysis reaction

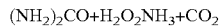

The $NH_3$ reacts preferably with NOx in the SCR converter to become $N_2$ and $H_2O$ according to the de-NOx reaction

The unused $NH_3$ is expelled from the SCR and is monitored by $NH_3$ sensor 12. The $NH_3$ value determined by sensor 12 is used in the urea's dosing algorithm controlled by ECU 16 to maximize the SCR efficiency and minimize or avoid altogether the escape of $NH_3$ (ammonia slip) into the ambient atmosphere.

SCR catalyst 28 includes upstream gas sampling sensor 30 and downstream gas sampling sensor 32, upstream temperature sensor 34 and downstream temperature sensor 36, and temperature difference (ΔT) sensor 38. Urea dosing pump 40 controls (via instructions from ECU 16) the quantity of reducing agent 42 delivered to the exhaust gases entering SCR catalyst 28 via control valve 44 and coupled to a source of compressed air 46 delivered via air atomizing nozzle 48. Dosing pump 40 pressurizes the reducing agent 42 via the compressed air 46.

Ammonia sensor 12 is coupled to the exhaust manifold 18 downstream of the catalyst 28. Temperature sensors 34 and 36 provide a location specific indication of the temperature (T) of the SCR catalyst 28. Alternatively, catalyst temperature (T) could be estimated using methods know to those skilled in the art. Ammonia sensor 12 provides an indication of ammonia concentration ($NH_3$) to controller 16 for determining a control signal sent to control valve 44.

Controller 16 is shown in block diagram form in FIG. 1 and is understood to include, for example, components found in a conventional microcomputer including a microprocessor unit, input/output ports, read-only memory, random access memory, and a data bus. The controller 16 receives various signals from sensors coupled to the engine 14, in addition to those signals discussed in detail herein, including engine coolant temperature such as from a temperature sensor coupled to a cooling sleeve, a measurement of manifold pressure (MAP) from a pressure sensor coupled to an intake manifold, a measurement (T) of manifold temperature from a temperature sensor, an engine speed signal (RPM) from an engine speed sensor coupled to a crankshaft.

Figure 2:
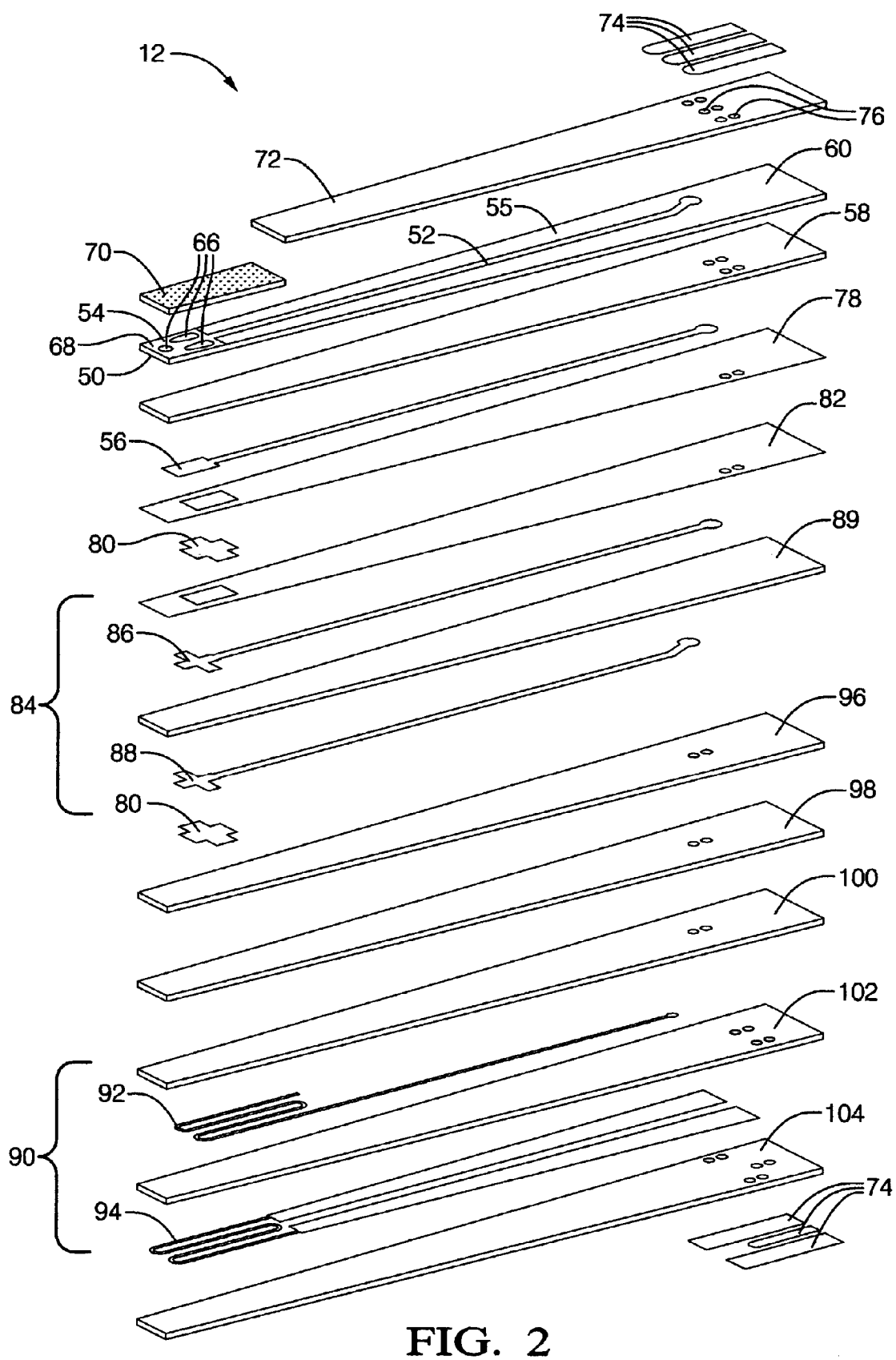
FIG. 2 is an exploded view of a sensing element including a species selective (ammonia) sensor.
Figure 3:
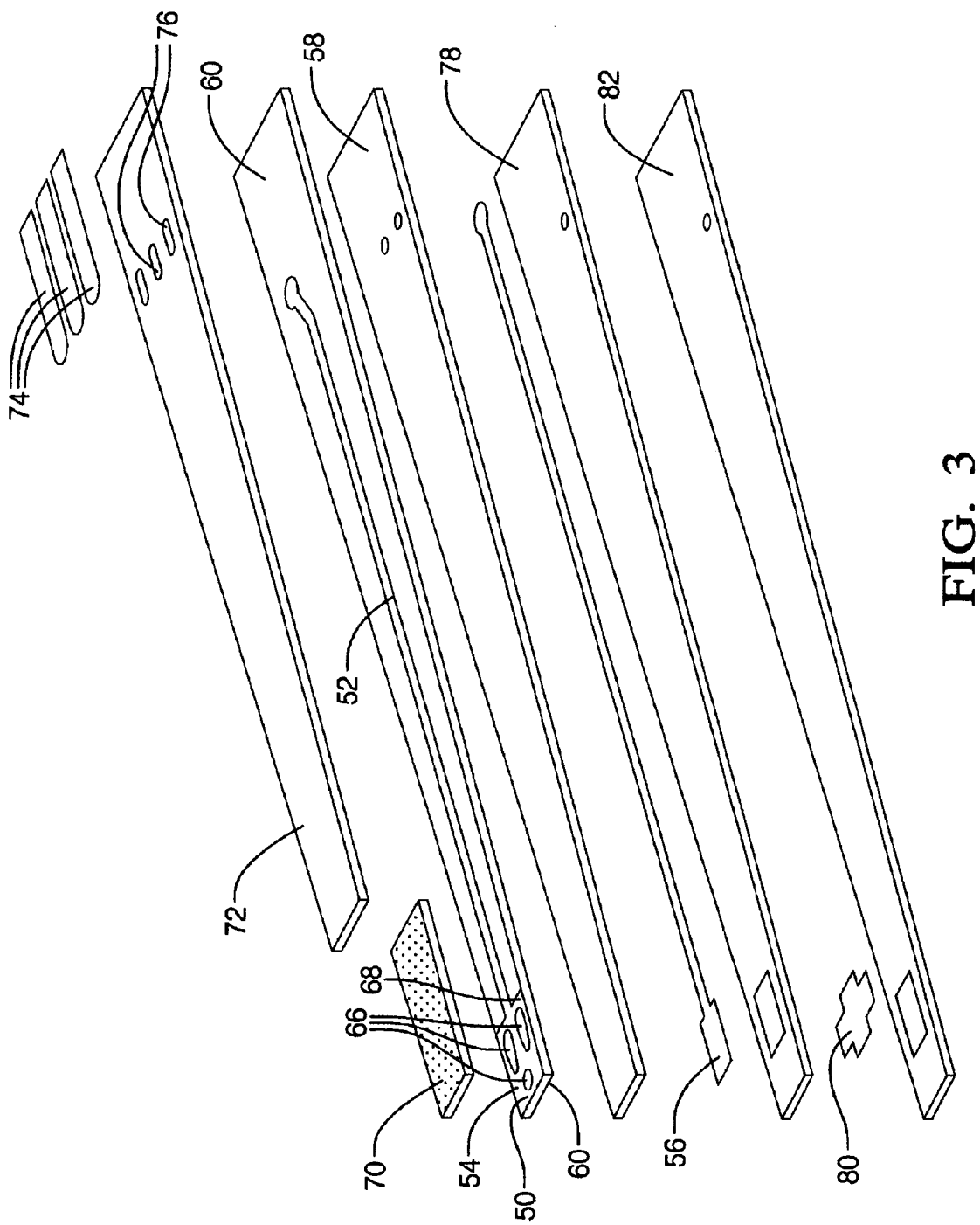
FIG. 3 is an enlarged, exploded view of a portion of the species selective sensor of FIG. 2.
Figure 10:
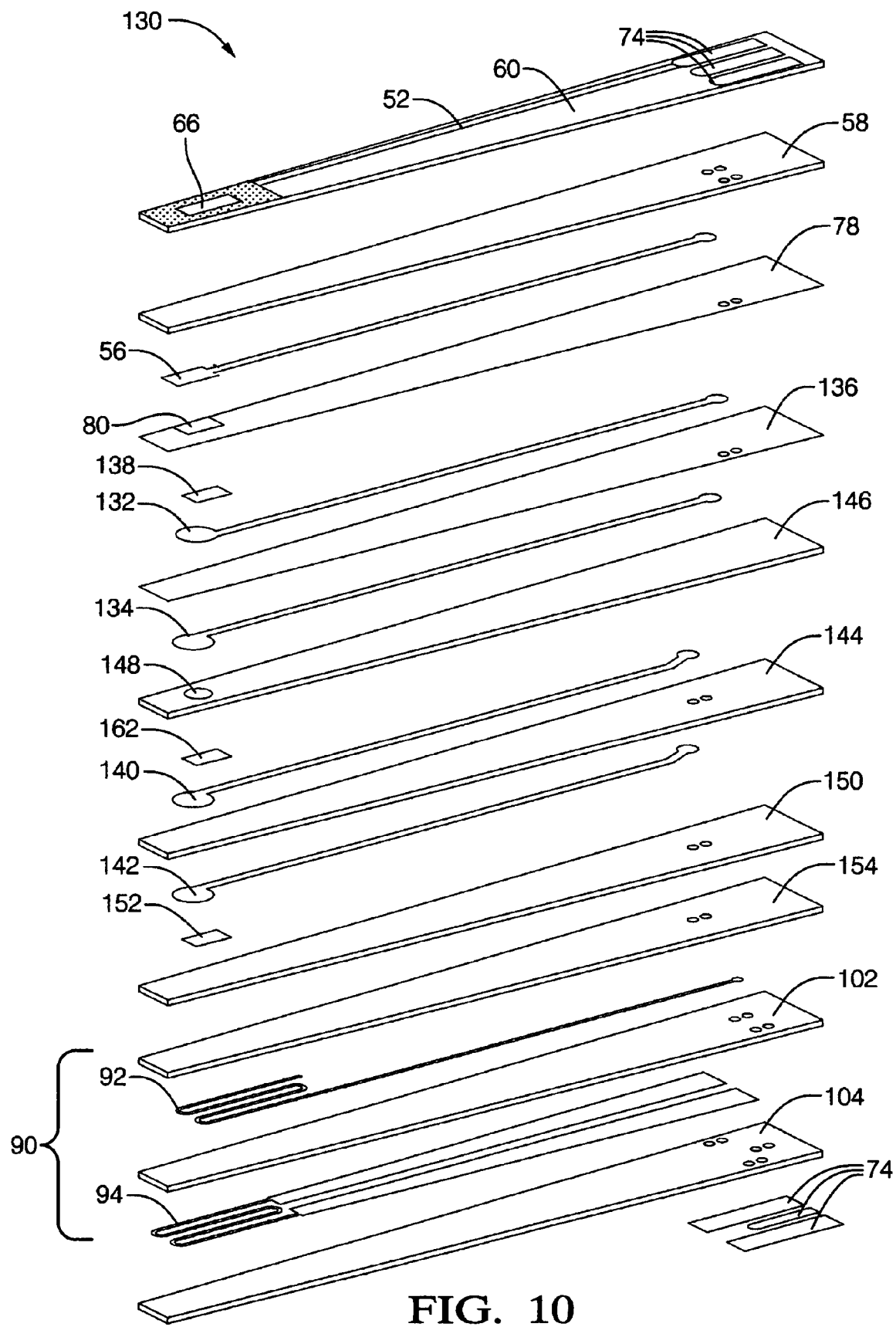
FIG. 10 is an exploded view of a sensing element including an air fuel ratio sensor.

A sensing element 12 comprising a species selective (for example, ammonia/$NH_3$) sensor, a heater, a temperature sensor, and optionally an air to fuel (A/F) ratio sensor (a sensing element including an A/F sensor is shown in FIG. 10) is illustrated in FIGS. 2 and 3 (a close-up, exploded view of a portion of sensing element is shown in FIG. 2). Sensing element 12 includes $NH_3$ sensor comprising species selective electrode, for example, ammonia selective ($NH_3$) electrode 50 and reference electrode 56 disposed on opposite sides of a solid electrolyte (doped zirconia) layer 58. The reference electrode (or counter electrode of the $NH_3$ sensing oxide electrode) 56 can be printed on the opposite side of the doped zirconia layer 58 opposite the ammonia selective electrode 50.

Separating the solid electrolyte layer 58 from species selective electrode 50 is an insulating (alumina) layer 60 having a section 54 including an opening pattern (a hole or holes) 66 and a dense or solid section 55. Insulating layer 60 comprises, a dielectric material, such as, for example, alumina, cordierite, lanthanum oxide, spinel, titania, yttrium oxide, and the like, as well as combinations comprising at least one of the foregoing dielectric materials. Optionally, section 54 comprises a porous section and section 55 comprises a dense or solid section. If section 66 is selected to be porous, the porosity must be sufficient to enable the deposited first material of the $NH_3$ sensing electrode to make contact with the bottom electrolyte 58.

Species selective electrode 50 is disposed on alumina layer 60 on a side opposite electrolyte layer 58 and includes non-active electrode lead portion (e.g., platinum) 52 disposed over section 55 on layer 60 and species selective sensing electrode portion 68 comprising an $NH_3$ sensing oxide disposed over area 54 so as to form an electrical connection with non-active lead portion 52 and the surface of solid electrolyte of 58 by way of opening 66. The deposition of 52 on layer 60 is such that it surrounds the open area 66 to its periphery but not in contact with the surface of electrolyte 58.

As best seen in FIG. 3, the sensing oxide layer 68 is disposed so as to contact the electrolyte layer 58 through opening pattern (holes) 66 in insulation layer 60. In this fashion, the $NH_3$ electrode sensing portion 68 contacts the electrolyte layer 58 and makes the electrical connection to the non-active $NH_3$ electrode portion 52. Both $NH_3$ sensing electrode portion 68 and the reference electrode 56 are exposed to the same ambient sensing atmosphere/exhaust atmosphere while non-active electrode lead portion 52 does not directly contact the electrolyte layer 58 thereby avoiding loss of emf signal.

A protective coating layer 70 can optionally be disposed over the $NH_3$ sensing oxide 68. Alternately, or in addition to the protective coating layer 70, an insulating and/or protective layer 72 is disposed over $NH_3$ electrode 52. Electrical contact with electrode pad 74 is made by lead portion 52 through vias 76 in insulating layer 72 so that the emf signal can be detected from outside.

Another insulating layer 78 is disposed on the side of the reference electrode 56 opposite the solid oxide layer 58. Insulating layer 78 enables fluid communication between the reference electrode 56 and the exhaust gas. Gas channel/aperture 80, disposed between insulating layer 78 and insulating layer 82, is in fluid communication with the reference electrode 56 and with the ambient atmosphere and/or the exhaust gas.

Disposed on a side of the gas channel 80 opposite the reference electrode 56 is a temperature sensor 84 including first temperature sensing electrode 86 and second temperature sensing electrode 88 disposed on opposite sides of an electrolyte layer 89.

Further disposed on a side of the reference electrode 56 opposite the solid oxide electrolyte layer 58 is a heater such as heater 90 including electromagnetic shield (EM) 92 disposed on dielectric layer 102 and heating element 94 disposed on dielectric layer 104. The heater is in communication with temperature sensor 84 for maintaining sensing element 12 at the desired operating temperature. The heater can be any conventional heater capable of maintaining the sensor at a sufficient temperature to facilitate the various electrochemical reactions therein. The heater, which is typically platinum, platinum-alumina, palladium, and the like, as well as mixtures and alloys comprising at least one of the foregoing metals, or any other conventional heater, is generally screen printed onto a substrate to a thickness of about 5 microns to about 50 microns, although not limited. Typically, one or more insulating layers such as insulating layers 82, 96, 98, 100, 102, and 104 are disposed between the reference gas electrode and the heater as well as on a side of the heater opposite the reference gas channel 80. Furthermore, in addition to the protective layers, electrodes and leads thereto, heater, electrolyte layers and dielectric layers, additional conventional components can be employed in the sensing element, including but not limited to, additional protective coatings, for example, spinel, alumina, cordierite, magnesium aluminate, and the like, as well as combinations comprising at least one of the foregoing coatings, lead or $SO_2$ getter layer(s), ground plane(s), support layer(s), additional electrochemical cell(s), and the like.

Formation of the gas sensors described herein can be accomplished in any conventional fashion, for example, forming the individual layers of the sensor, firing the layers, and stacking the layers to form the sensor, or forming the green layers, stacking the layers, and co-firing to produce the sensor. For example, the protective layers, alumina layers, and solid electrolyte layers are formed using a doctor blade tape forming method. The desired vias are formed in these layers accordingly. Holes are also formed in the protective layers, alumina layers, and electrolyte layers using a punching or machining technique.

Thick film multi-layer sensor forming technology may be used to prepare the sensing elements. For example, alumina and yttria-alumina doped zirconia is made into a slurry and cast as standard thickness green tapes, i.e., about 200 microns thick. Heater, electrodes, electrode leads, and pads are printed onto the green tapes and the printed green tapes are thermally laminated, cut, and fired at about 1450° C. to about 1500° C. for about 2 hours. The species selective electrode materials are then screen printed on and fired at lower temperatures, that is, about 750° C. to about 900° C. The prepared sensing elements are then ready for evaluation.

Figure 4:
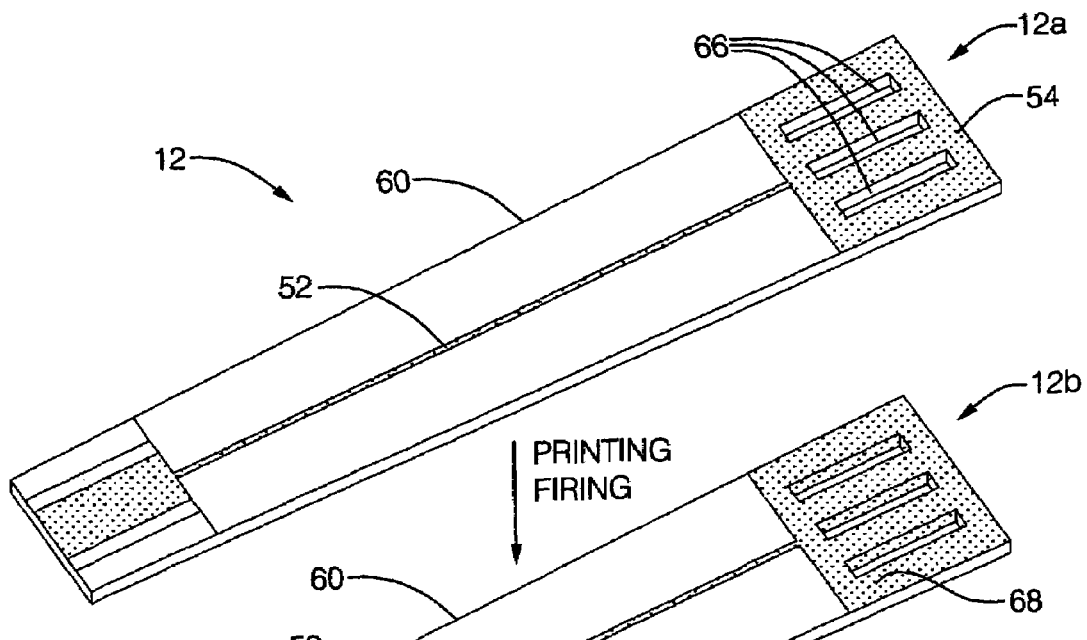
FIG. 4 is a top view of a sensing element before and after a species selective sensing material and non-active electrode portion are printed onto an insulating layer and fired.

FIG. 4 illustrates forming steps for preparing sensing element 12 before the species selective electrode sensing material 68 is printed (12a) over non-active electrode lead portion 52 and after the species selective electrode (sensing oxide) material 68 has been printed (12b) over area 54 and fired.

Figure 5:
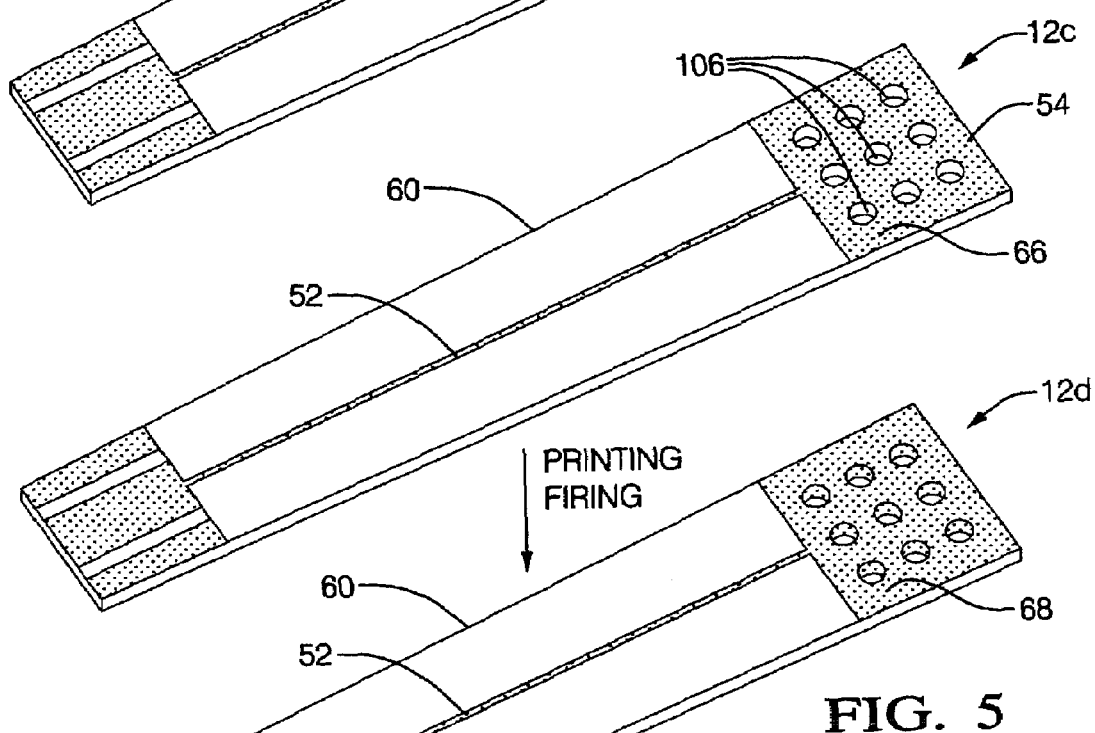
FIG. 5 is a top view illustrating an alternate embodiment of the sensing element wherein the opening pattern through which the species selective sensing material makes contact with the solid electrolyte layer comprises a plurality of circular openings and showing the sensing element after a species selective sensing material and non-active electrode lead portion has been printed onto an insulating layer and fired.
Figure 6:
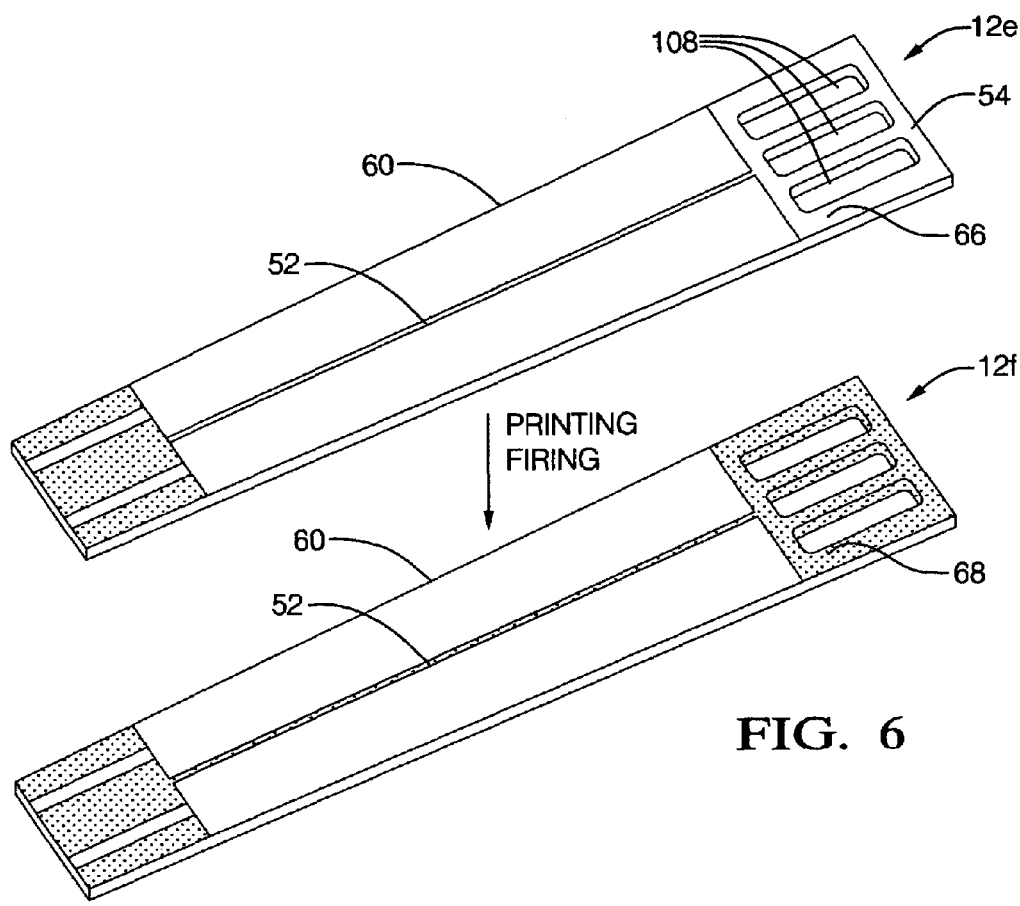
FIG. 6 is a top view illustrating yet another embodiment of the sensing element wherein the opening pattern through which the species selective sensing material makes contact with the solid electrolyte layer comprises a plurality of rounded rectangular channels and showing the sensing element after a species selective sensing material and non-active electrode lead portion has been printed onto an insulating layer and fired.

The opening pattern configuration for insulating (alumina) layer 60 is not limited, but rather numerous geometric configurations for opening pattern 66 are contemplated provided the opening pattern is sufficient to create a periphery enabling good electrical contact between the sensing oxide portion 68 of species selective electrode 50 and the lead portion 52 without causing contact between electrolyte layer 58 and lead portion 52 of species selective electrode 50. For example, the opening pattern can comprise a circular opening, a plurality of circular openings, a rectangular opening, a plurality of rectangular openings, a generally rectangular rounded end opening, a plurality of generally rectangular rounded end openings, other geometric patterns, or a combination thereof. FIGS. 5 and 6 illustrate two possible embodiments for opening pattern 66. FIG. 5 shows a sensor 12c before printing with a species selective sensing material and before firing. Sensor 12c includes insulation layer 60 having disposed thereon $NH_3$ non-active electrode lead portion 52 and having area 54 with insulating layer 60 having an opening pattern 66 comprising a plurality of circular openings 106. Sensing oxide layer 68 is printed over the area 54 and opening pattern 66 and fired to provide sensor 12d.

FIG. 6 shows another embodiment including a sensor 12e before printing with a species selective sensing material and before firing. Sensor 12e includes insulation layer 60 having disposed thereon non-active $NH_3$ electrode lead portion 52 and having an area 54 and an opening pattern 66 comprising a plurality of generally rectangular, rounded ended openings 108. Sensing oxide layer 68 is printed over area 54 and opening pattern 66 and fired to provide sensor 12f.

Insulating layers and any support layers, are typically capable of providing structural integrity (for example, effectively protecting the gas sensor from abrasion, vibration, and the like, and providing physical strength to the sensor), and physically separating and electrically isolating various components. The insulating layer or layers, which can be formed using ceramic tape casting methods or other methods such as plasma spray deposition techniques, screen printing, stenciling and other techniques conventionally used in the art, can each be up to about 200 microns thick, with a thickness of about 50 microns to about 200 microns preferred. In order to reduce the leakage current, high resistance dielectric materials should be employed, for example, materials, which at temperatures of about 800° C. have a current leakage of less than about 0.01 microamperes. Since the materials employed in the manufacture of gas sensors preferably comprise substantially similar coefficients of thermal expansion, shrinkage characteristics, and chemical compatibility in order to minimize, if not eliminate, delamination and other processing problems, the particular material, alloy or mixture chosen for the insulating layer is dependent upon the specific electrolyte employed. For example, these insulating layers can comprise a dielectric material, such as alumina, spinel, cordierite, magnesium aluminate, lanthanum oxide, strontium oxide, titania, strontium titanate, barium titanate, and the like, as well as combinations comprising at least one of the foregoing dielectric materials.

The electrolyte layer 58 is in embodiments a solid electrolyte that can comprise the entire layer or a portion thereof. The electrolyte layer can be any material that is capable of permitting the electrochemical transfer of ions while inhibiting the physical passage of exhaust gases and is compatible with the environment in which the gas sensor will be utilized (for example, up to about 1,000° C.). Possible solid electrolyte materials can comprise any material conventionally employed as sensor electrolytes, including, but not limited to, zirconia which may optionally be stabilized (or doped) with calcium, barium, yttrium, magnesium, aluminum, lanthanum, cesium, gadolinium, and the like, as well as combinations comprising at least one of the foregoing. For example, the electrolyte can be alumina and yttrium stabilized zirconia. Typically, the solid electrolyte, which can be formed via many conventional processes (e.g., die pressing, roll compaction, stenciling and screen printing, tape casting techniques, and the like), has a thickness of up to about 500 microns, particularly a thickness of approximately 25 microns to about 500 microns or about 50 microns to about 200 microns.

The electrolyte layer 58, protective layer or insulating layers such as layers 70, 72, etc., can comprise the entire layer or any portion thereof. For example, they can form the layer, be attached to the layer (protective material/electrolyte abutting a dielectric material), or disposed in an opening in the layer (protective material/electrolyte can be an insert in an opening in a dielectric material layer). The latter arrangement eliminates the use of excess electrolyte and protective material, and reduces the size of gas sensor by eliminating layers. Any shape can be used for the electrolyte and insulating layers, with the size and geometry of the various inserts, and therefore the corresponding openings, is dependent upon the desired size and geometry of the adjacent electrodes. It is preferred that the openings, inserts, and electrodes have a substantially similar geometry.

The $NH_3$ species selective electrode materials comprise oxide powders, doped oxide powders, and mixtures thereof, including, but not limited to, for example, binary or ternary oxide materials such as vanadium oxides, and mixtures thereof. Representative $NH_3$ selective electrode materials include, for example, $V_2O_5$, $WO_3$, $MoO_3$, $BiVO_4$, $BiTaO_4$ as well as materials listed in Table 1, below.

TABLE 1

| Alkaline Group | | | | | |
|---|---|---|---|---|---|
| $LiVO_3$ | $NaVO_3$ | $Na_3VO_4$ | $KVO_3$ | $K_3VO_4$ | $Cs_3VO_4$ |
| $MgV_2O_6$ | $Mg_2V_2O_7$ | $Mg_2V_6O_{17}$ | $Mg_5V_4O_{13}$ | $Mg_3V_2O_8$ | $CaV_2O_6$ |
| $Ca_3V_2O_8$ | $SrV_2O_6$ | $Sr_2V_2O_7$ | $Sr_3V_2O_8$ | | |
| Alkaline Earth Group | | | | | |
| $MgV_2O_6$ | $Mg_2V_2O_7$ | $Mg_2V_6O_{17}$ | $Mg_5V_4O_{13}$ | $Mg_3V_2O_8$ | $CaV_2O_6$ |
| $Ca_3V_2O_8$ | $SrV_2O_6$ | $Sr_2V_2O_7$ | $Sr_3V_2O_8$ | | |
| Transition Group | | | | | |
| $CuV_2O_6$ | $Ni_3V_2O_8$ | $NiV_2O_6$ | $CdV_2O_6$ | $Cd_2V_2O_7$ | $Cd_3V_2O_8$ |
| $CrVO_4$ | $Co_3V_2O_8$ | $Pb_3V_2O_7$ | $CuV_2O_6$ | $Cu_5V_2O_{10}$ | $AgV_7O_8$ |
| $FeVO_4$ | $CeVO_4$ | $MnVO_3$ | $Mn_2V_2O_7$ | $Zn_4V_2O_9$ | $Zn_3V_2O_8$ |
| $Zn_2V_2O_7$ | $ZnV_2O_6$ | $TiVO_4$ | | | |
| Rare Earth Group | | | | | |
| $GdVO_4$ | $LuVO_4$ | $ErVO_4$ | $DyVO_4$ | $HoVO_4$ | $YVO_4$ |
| $TmVO_4$ | $YbVO_4$ | $TbVO_4$ | $SmVO_4$ | $NdVO_4$ | |
| Other | | | | | |
| $AlVO_4$ | $TeVO_4$ | $SbVO_4$ | | | |

In embodiments, the oxides comprise dopants selected to increase conductivity or enhance sensitivity. For example, dopants include, but are not limited to, elements, such as Ce, Pb, Ag, Mn, Mo, W, Ca, Li, Na, K, Cs, Zr, Ge, Sb, Mg, Sr, Sc, Ti, Nb, Fe, Co, Ni, Cu, Rh, Pd, Ga, In, and Sn, and mixtures and combinations thereof. Typically, for an about 10 gram to an about 50 gram quantity of powder such as $BiVO_4$ based sensing oxides, the selected quantity of oxide powder is ground for about 5 minutes, fired at about 800° C. to about 850° C. overnight, ground again for about 5 minutes, and fired at about 800° C. to about 850° C. overnight. The powder is ground again and made into ink paste. The electrodes are screen printed and fired at about 800° C. to about 850° C. for about 30 to about 60 minutes. The $NH_3$ selective electrode can also be formed using techniques such as the aforementioned screen printing, sputtering, chemical vapor deposition, painting, stenciling, among others.

The non-active electrode lead portion 52 will contact the $NH_3$ sensing oxide 68 and alumina layer 60 but not the doped zirconia layer 58. The emf signal comes from $NH_3$ sensing oxide 68 that contacts the doped zirconia 58 and conducts to the non-active platinum electrode 52 and to the outside. The $NH_3$ sensing relies on the contact of the $NH_3$ sensing oxide material 68 with the solid electrolyte 58. The presence of precious metal in direct contact with the electrolyte 58 will dampen the $NH_3$ sensing. However the $NH_3$ sensing oxide material 68 is not very conductive. In order to get the EMF out, platinum is disposed in close contact with the $NH_3$ sensing oxide material 68. Again the platinum 52 is not disposed in contact with the electrolyte 58 and should be non-active in terms of catalytic oxidation effect (otherwise the $NH_3$ would be oxidized before it was sensed down at the sensing oxide 68-electrolyte 58 contact area). Therefore, the non-active platinum electrode 52 is disposed on the insulation layer 60 but closely adjacent to the periphery of the opening 66 where $NH_3$ sensing oxide 68 will be deposited to make contact of the solid electrolyte 58 and with the non-active platinum electrode 52. In this way the contact area between the non-active platinum 52 and the $NH_3$ sensing oxide 68 is maximized so as to reduce the contact resistance. Further, the $NH_3$ sensing emf can be measured from the pad area 74 without too much of the emf being lost to overcome the $NH_3$ sensing oxide's internal resistance.

The non-active electrode portion 52 comprises, for example, a paste made of platinum and alumina so that it is not a good electrode for a typical exhaust oxygen sensor. Suitable inks include, but are not limited to, typical platinum inks used for exhaust oxygen sensor lead wires or contact pads, which have alumina additive and are not porous, including, but not limited to, for example, metals such as the aforementioned platinum, palladium, osmium, rhodium, iridium, gold, ruthenium zirconium, yttrium, cerium, calcium, aluminum, zinc, lanthanum, strontium, cobalt, perovskite, and the like, other materials, such as silicon, and the like, as well as oxides, mixtures, alloys, and cermets comprising at least one of the foregoing, and mixtures and combinations thereof. The addition of alumina to the ink allows one to make the non-active electrode very compact, dense and non-reactive with oxygen and $NH_3$ (otherwise which would catalyze $NH_3$ into $H_2O$ and $N_2$). If such oxidation reaction occurs, the $NH_3$ emf will decrease or disappear. Even though this non-active electrode has minimum catalytic reactivity, it should not be in direct contact with doped zirconia 58, to avoid decreasing or eliminating the $NH_3$ sensing signal.

Electrodes other than the non-active electrode 52 such as reference electrode 56 and temperature sensing electrodes 86 and 88, etc. can comprise, but are not limited to, materials typically used in exhaust oxygen sensors such as metals including platinum, palladium, osmium, rhodium, iridium, gold and ruthenium; metal oxides such as zirconia, yttria, ceria, calcia, alumina and the like; other materials, such as silicon, and the like; and mixtures and alloys comprising at least one of the foregoing. As with the electrolyte layer 58, the electrodes 52, 56, 86, 88 can be formed using conventional techniques. Some possible techniques include sputtering, chemical vapor deposition, screen printing, and stenciling, among others. If a co-firing process is employed for the formation of the sensor, screen printing the electrodes onto appropriate tapes is preferred due to simplicity, economy, and compatibility with the co-fired process. For example, reference electrode 56 can be screen printed over the solid electrolyte layer 58, while non-active electrode lead portion 52 and $NH_3$ sensing electrode portion 68 can be screen printed over insulating layer 60.

Exemplary sensors were prepared by thick-film multi-layer technology wherein an alumina tape having an opening pattern lays on top of a doped zirconia tape. The open area allows the $NH_3$ sensing oxide to be in contact with doped zirconia. The remaining area (non-$NH_3$ sensing oxide area) of the alumina layer can be covered with non-active platinum electrode, with the $NH_3$ sensing oxide overlaying or contacting the non-active platinum electrode to make the electrical connection between these two electrodes.

The sensing performance of the $NH_3$ sensing electrode 50, particularly $NH_3$ sensing response time, is dependent on the local electrode structure of the $NH_3$ sensing oxide electrode.

The response time is dependant on the $NH_3$ species gas diffusion path within the electrode. The sooner the $NH_3$ can get into and out of the electrolyte-$NH_3$ sensing-oxide area, the faster the response time.

The porosity and thickness of the $NH_3$ sensing oxide electrode (which in turn is determined by the thickness of layer 60) further determine the $NH_3$ sensing response time of the sensors.

Figure 7:
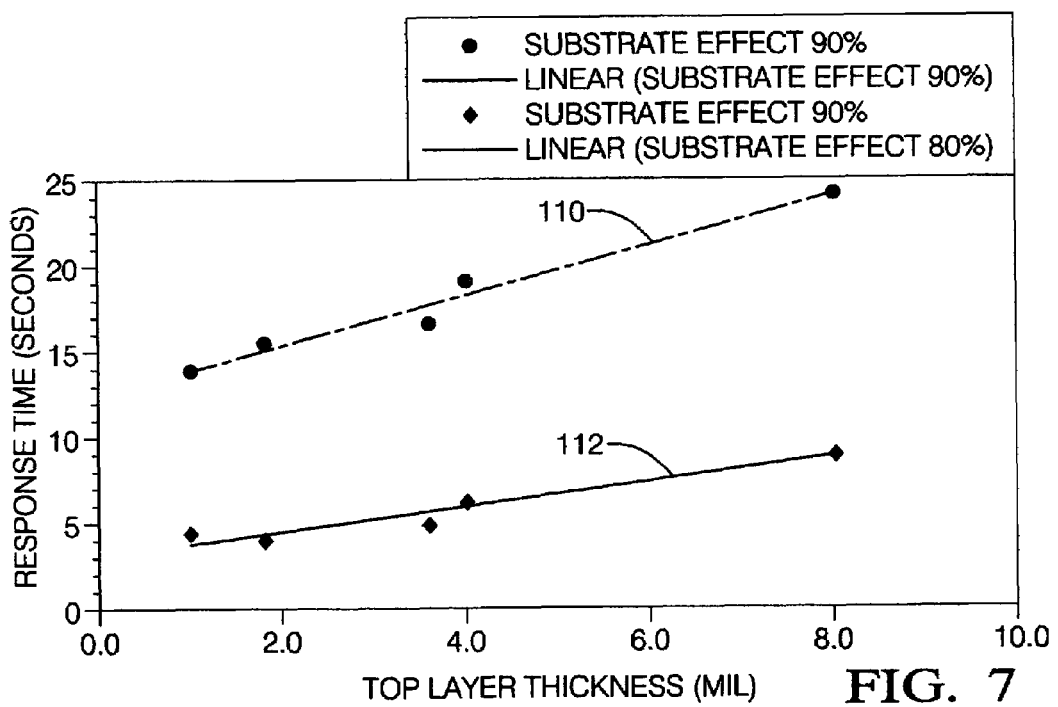
FIG. 7 is a graph illustrating response time (in seconds) versus top (alumina) layer thickness for ammonia sensing.
Figure 8:
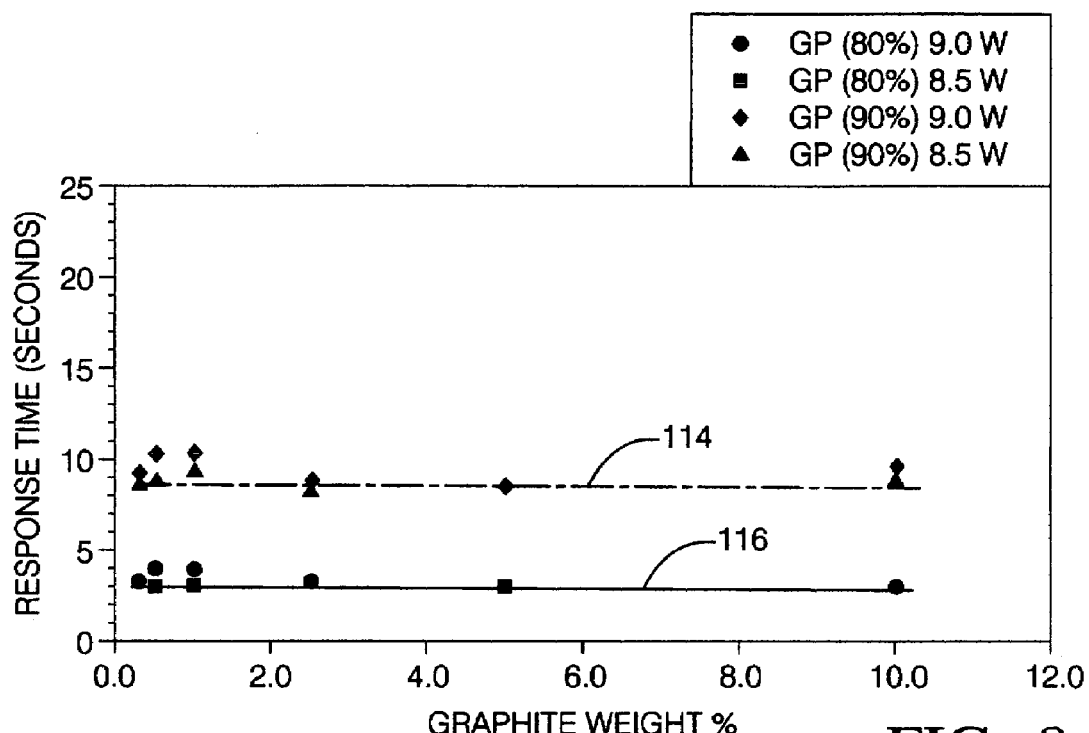
FIG. 8 is a graph illustrating response time (in seconds) versus weight percent of graphite additive in the $NH_3$ sensing oxide electrode.
Figure 9:
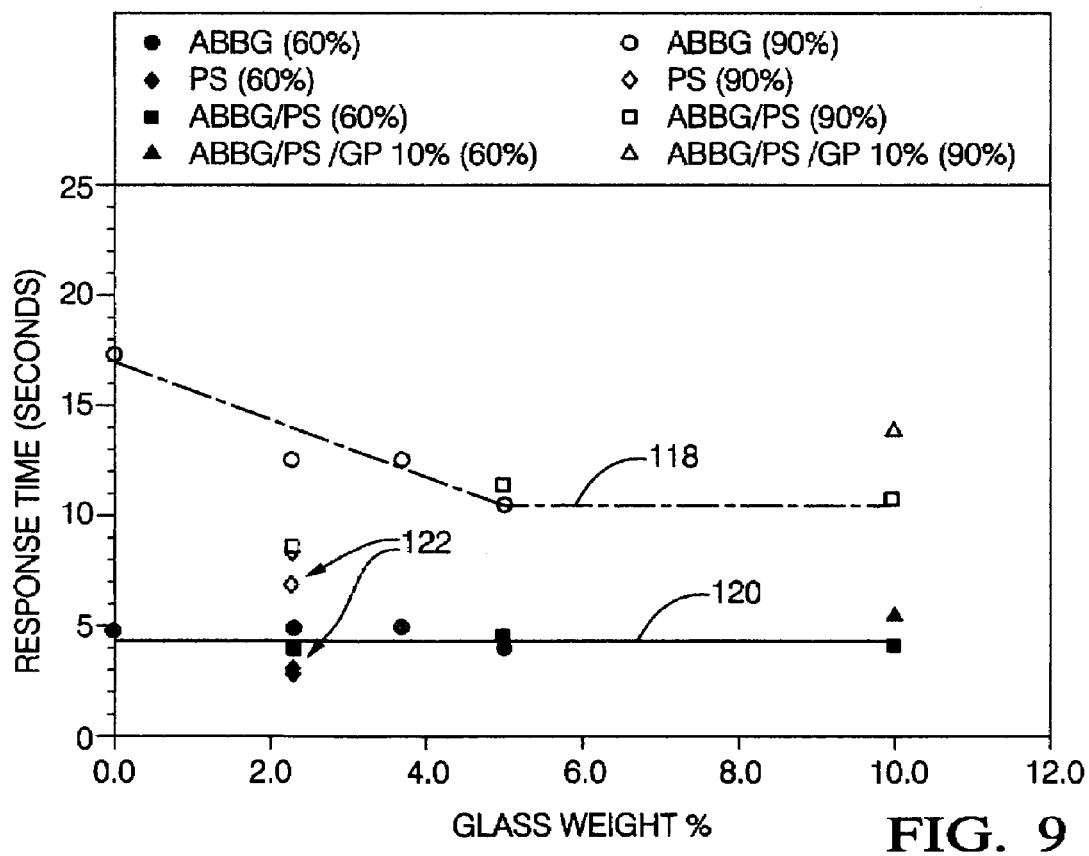
FIG. 9 is a graph illustrating response time (in seconds) versus weight percent of glass powder additive in the $NH_3$ sensing oxide electrode.

The example sensing elements tested as shown in the illustrations of FIGS. 7 through 9 were prepared in accordance with the structure shown in FIGS. 2 and 4. The $NH_3$ sensing oxide material was $BiVO_4$ doped with 5 atomic % of Mg. The fabricated sensors were inserted in a manifold which was mounted on top of a furnace where the sensing gas was introduced. The furnace was kept at a constant temperature of about 226° C. An air-nitrogen mixture was used as the basic carrier gas. Various gas species are added to the gas mixture before introduction into the furnace. A water bubbler was used to introduce moisture to the gas mixture. The $NH_3$ and NOx gas were added into the gas after the gas passes the water bubbler. The response time experiments were carried out with a gas flow rate of about 200 to about 400 cubic centimeters (cc) per minute. The response time was measured at 60% and 90% of the change of the emf signal strength due to a $NH_3$ switch between 100 parts per million (ppm) and 50 ppm of $NH_3$. The background gas was 1.5% $H_2O$ and 13% $O_2$ with the remainder being $N_2$. The heater is set at 8 W (wattage) or 9 W. The response time did not change much in this test range of wattage.

FIG. 7 illustrates response time in seconds (y-axis) versus alumina layer thickness of layer 60 in mil (x-axis) (wherein one thousandth of an inch is a mil) for samples fabricated with five different thicknesses of alumina green tapes (thickness of layer 60). The thicknesses were 1 mil, 1.8 mil, 3.6 mil, 4.0 mil and 8 mil. Thickness was measured while the alumina tapes were in the green stage (not yet fired or sintered). After sintering at 1450° C. for two hours, the tapes retained 80% of original thickness. The $BiVO_4$ (doped with 5 atomic % Mg) oxide electrodes were deposited and fired in air at 800° C. for one hour. The sensors were exposed to two different $NH_3$-containing gas mixtures; one having 100 parts per million $NH_3$ and the other 50 parts per million $NH_3$. The duration time of the emf between 0 and 60% and 90% of the final emf changes were measured and plotted as shown in FG. 7. Those circles surrounding line 110 represent the 90% signal strength response time. The circles surrounding the line 112 represent 60% of signal strength response time. As can be seen in FIG. 7, the thinner the tape, the faster the response time. This effect starts to saturate at a thickness of about 2 mil. The results indicate the response time is a function of the thickness of the oxide electrode, which is determined by the thickness of the layer 60 used. In this study, there were no special additives added to the electrode to create porosity in the oxide electrodes.

Additives for creating or enhancing open porosity in the $NH_3$ sensing oxide electrode can be added to improve response time, for example, even when a thick layer 60 is used. Suitable additives include, but are not limited to, for example, graphite, carbons, open porous glass powder, silica glass powder, regular glass powder, alkali barium borosilicate, and mixtures and combinations thereof. Examples of response times achieved with sensors including such additives are shown in FIGS. 8 and 9.

FIG. 8 illustrates the effect of graphite additive on response time. The data were plotted in seconds (y-axis) versus graphite weight % (x-axis). The samples were fabricated with 3.6 and 4.0 mil alumina tapes for the layer 60. After sintering at 1450° C. for two hours, the tapes retained 80% of their original thickness. $BiVO_4$ doped with 5 atomic % of Mg was used as the starting oxide electrode material. Graphite was added into the 5% Mg doped $BiVO_4$ powder and then made into ink paste. The weight % of graphite were 0.33%, 0.66%, 1.0%, 2.5%, 5%, and 10% (100 weight % equals the weight of 5% Mg doped $BiVO_4$ powder). The ink paste was deposited and fired in air at 800° C. for 1 hour. Response times were measured at 60% (see line 116) and 90% (see line 114) of the changes of the signal strength when $NH_3$ concentration was changed from 100 parts per million to 50 parts per million.

Additional example sensors were prepared and tested with the results shown in FIG. 9. The examples were all fabricated with 3.6 mil thick alumina tape (60). After sintering at 1450° C. for two hours, the tapes retained 80% of their original thickness. Again the powder comprising BiVO4 doped with 5 atomic % Mg was used as the base electrode material. We studied the effect of alkali barium borosilicate glass (ABBG) on sensor response time. The glass composition comprised 64% $SiO_2$, 8% $Al_2O_3$, 19% $B_2O_3$, 3% $K_2O$, 2% $Na_2O$, 3% BaO, and 1% $Li_2O$, by weight. We added 0%, 2.3%, 3.7% and 5.0%, by weight, into ABBG glass powder with $BiVO_4$ (5% Mg) powder. The inks were deposited to form electrodes and fired at 800° C. in air for 1 hour. Response times were measured at 60% (see line 118 in FIG. 9) and 90% (see line 120 in FIG. 9) of the changes of the signal strength when $NH_3$ concentration was changed from 100 parts per million to 50 parts per million. As shown in FIG. 9, the greater amount of borosilicate glass added, the faster the response time.

FIG. 9 further illustrates the effect of porous silica (PS) glass powder on the sensor response time. The PS glass composition is 96% $SiO_2$, 3% $B_2O_3$, 0.4% $Na_2O$, 3% BaO, and less than 1% $Al_2O_3$, by weight. The void space was 28% by volume for this glass powder. The studied weight % shown in FIG. 9 was 2.3. The 60 and 90% response data were plotted as the open and solid diamonds, respectively, as indicated by the reference numeral 122 in FIG. 9. We also studied the combined effect of ABBG glass powder and PS powder on sensor response time. Equal amounts of both powders (at 2.3%, 5% and 10% by weight individually) were tested. The results are represented by the solid and open squares in FIG. 9. We also tested the effect of 10 weight % of ABBG, PS, and graphite powders (total 30 weight %) on sensor response time. The results are represented by the solid and open triangles in FIG. 9.

The addition of glass powders that have low softening temperatures (i.e., softening temperatures of about 550° C. to about 850° C.) such as, but not limited to, alkali barium borosilicate glass (ABBG), can be employed to further hold down the $NH_3$ sensing oxide materials against the doped zirconia and non-active platinum electrode. The mechanism provides long term durability without losing the $NH_3$ sensing oxide powder to the mechanical vibrations encountered in the engine exhaust environment.

The protective coating layer 70, provides protection against the poisoning soot in the exhaust gas and holds back the oxide electrode from detaching from the doped zirconia.

The present sensors employed in the urea-SCR system can decrease exhaust NOx emissions by about 65% to about 90%. The sensors are based on non-equilibrium Nerstian electrochemical principle. The sensors measure $NH_3$ and output an electromotive force (emf) signal that is proportional to the logarithm of the $NH_3$ partial pressure. The sensors are free of NO, CO and hydrocarbon (HC) interference. Both $NO_2$ and $SO_2$ have an interference effect on the $NH_3$ emf output. Because of this, the amount of $NO_2$ and $SO_2$ present in the exhaust after the SCR should be kept under about 200 parts per million (ppm) and 30 ppm, respectively. Oxygen and steam (H₂O) are known to interfere with the emf output also. This effect can be corrected if the air to fuel ratio (A/F) of the exhaust gas is known. Determination of the A/F is achieved, for example, by inputting the A/F information from the engine ECM or building an A/F sensor together with the $NH_3$ sensor. The $NH_3$ sensors use ceramic flat plate technology, provide greater than about ±5% accuracy and are particularly suitable for use with on-board diagnostic and de-NOx SCR systems.

Multi-sensing functions can be built into the sensor. For example, to monitor air to fuel ratio (A/F) of the exhaust, as shown in FIG. 10, an A/F sensor can be built into the same structure as the sensing element. In such a case, an additional electrolyte layer is added, with oxygen pump electrodes attached on both sides of the electrolyte layer. A gas-diffusion-limiting aperture is installed to limit the pump current. The pumping current will be linearly proportional to the oxygen concentration of the exhaust gas. FIG. 10 illustrates an embodiment of a sensor 130 (wherein like elements are numbered alike as in FIGS. 2 and 3) having an air-fuel ratio sensing function including first and second air-fuel pump electrodes 132, 134 disposed on opposite sides of an electrolyte layer 136 including aperture 138 for the first air-fuel pump electrode 132. First and second air-fuel reference electrodes 140, 142 are disposed on opposite sides of electrolyte layer 144. An insulating layer or layers, such as insulating layer 146 including cavity opening 148 is disposed between the A/F pump cell and the air-fuel reference cell. Electrolyte layer 144 includes aperture 152 for second air-fuel reference electrode 142. Insulating layers 150 and 154 separate the air-fuel sensor component from heater 90 including electromagnetic shield 92 and heating element 94 disposed on insulating layers 102, 104. There is a diffusion-limiting aperture 162 which limits the gas diffusion to the emf electrode 140 and pump electrode 134.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A sensor comprising:
a species selective electrode and a reference electrode having an electrolyte layer disposed therebetween;
a reference gas channel in fluid communication with the reference electrode;
a heater disposed in thermal communication with the sensor;
a temperature sensor disposed in communication with the heater for maintaining the sensor at a desired operating temperature;
wherein the species selective electrode is disposed on a first side of an insulating layer separating the species selective electrode from the electrolyte, the insulating layer having a first substantially solid area and a second area having an opening pattern extending through the insulating layer;
the species selective electrode comprising a species sensing electrode portion comprising a first material disposed on the opening pattern of the insulating layer to extend inside at least one opening of the opening pattern so as to contact the electrolyte layer through the opening pattern and a non-active electrode lead portion comprising a second material that is different from the first material, the first material being deposited on top of the second material over the second area so that the non-active electrode lead portion is in electrical communication with the species sensing electrode portion, said non-active electrode lead portion disposed over the first substantially solid-area and the second area so as to substantially surround the periphery of at least one opening in the opening pattern while being sufficiently spaced from the periphery of each opening so as to be free from contact with the electrolyte layer; wherein both the species selective electrode and the reference electrode are in fluid communication with an exhaust atmosphere.

2. The sensor of claim 1, further comprising:
an air-fuel ratio sensor.

3. The sensor of claim 1, wherein the species selective electrode is an ammonia selective electrode.

4. The sensor of claim 1, wherein the species sensing electrode portion comprises oxide powders, doped oxide powders, binary oxide materials, ternary oxide materials, vanadium oxides, $V_2O_5$, $WO_3$, $MoO_3$, $BiVO_4$, $BiTaO_4$, $LiVO_3$, $NaVO_3$, $Na_3VO_4$, $KVO_3$, $K_3VO_4$, $Cs_3VO_4$, $MgV_2O_6$, $Mg_2V_2O_7$, $Mg_2V_6O_{17}$, $Mg_5V_4O_{13}$, $Mg_3V_2O_8$, $CaV_2O_6$, $Ca_3V_2O_8$, $SrV_2O_6$, $Sr_2V_2O_7$, $Sr_3V_2O_8$, $CuV_2O_6$, $Ni_3V_2O_8$, $NiV_2O_6$, $CdV_2O_6$, $Cd_2V_2O_7$, $Cd_3V_2O_8$, $CrVO_4$, $Co_3V_2O_8$, $Pb_3V_2O_7$, $CuV_2O_6$, $Cu_5V_2O_{10}$, $AgV_7O_8$, $FeVO_4$, $CeVO_4$, $MnVO_3$, $Mn_2V_2O_7$, $Zn_4V_2O_9$, $Zn_3V_2O_8$, $Zn_2V_2O_7$, $ZnV_2O_6$, $TiVO_4$, $GdVO_4$, $LuVO_4$, $ErVO_4$, $DyVO_4$, $HoVO_4$, $YVO_4$, $TmVO_4$, $YbVO_4$, $TbVO_4$, $SmVO_4$, $NdVO_4$, $AlVO_4$, $TeVO_4$, $SbVO_4$, or mixtures thereof.

5. The sensor of claim 4, wherein the species sensing electrode portion is doped with a material selected from the group consisting of Ce, Pb, Ag, Mn, Mo, W, Ca, Li, Na, K, Cs, Zr, Ge, Sb, Mg, Sr, Sc, Ti, Nb, Fe, Co, Ni, Cu, Rh, Pd, Ga, In, and Sn, and mixtures and combinations thereof.

6. The sensor of claim 1, wherein the species sensing electrode portion comprises an additive for creating or enhancing open porosity in the species selective sensing electrode.

7. The sensor of claim 1, wherein the species sensing electrode portion comprises an additive for creating or enhancing open porosity in the species selective sensing electrode portion selected from the group consisting of graphite, carbons, open porous glass powder, silica glass powder, regular glass powder, alkali barium borosiliate, and mixtures and combinations thereof.

8. The sensor of claim 1, wherein the non-active electrode lead portion comprises an alumina additive and optionally further comprises a material selected from the group consisting of platinum, palladium, osmium, rhodium, iridium, gold, ruthenium zirconium, yttrium, cerium, calcium, aluminum, zinc, lanthanum, strontium, cobalt, perovskite, silicon, oxides, mixtures, alloys, cermets, and mixtures and combinations comprising at least one of the foregoing.

9. The sensor of claim 1, wherein the opening pattern comprises a circular opening, a plurality of circular openings, a rectangular opening, a plurality of rectangular openings, a generally rectangular rounded end opening, a plurality of generally rectangular rounded end openings, or a combination thereof.

10. The sensor of claim 1, further comprising:
a protective coating layer disposed over the species sensing electrode portion of the species selective electrode.

11. A method for forming a sensor comprising:
disposing a species selective electrode and a reference electrode on opposite sides of an electrolyte layer;

forming a reference gas channel in fluid communication with the reference electrode;
disposing a heater in thermal communication with the sensor;
disposing a temperature sensor in communication with the heater for maintaining the sensor at a desired operating temperature;
disposing the species selective electrode on a first side of an insulating layer so as to separate the species selective electrode from the electrolyte layer, the insulating layer having a first substantially solid area and a second area having an opening pattern extending through the insulating layer;
the species selective electrode comprising a species sensing electrode portion comprising a first material disposed on the opening pattern of the insulating layer to extend inside at least one opening of the opening pattern so as to contact the electrolyte layer through the opening pattern and a non-active electrode lead portion comprising a second material that is different from the first material;
depositing the first material on top of the second material over the second area so that the non-active electrode lead portion is in electrical communication with the species sensing electrode portion, said non-active electrode lead portion disposed over the first substantially solid area and the second area so as to substantially surround the periphery of at least one opening in the opening pattern while being sufficiently spaced from the periphery of each opening so as to be free of contact with the electrolyte layer, to form a green sensor; and
firing or co-firing the green sensor.

12. The method of claim 11, further comprising:
disposing an air-fuel ratio sensor as part of the sensor.

13. The method of claim 11, wherein the species selective electrode is an ammonia selective electrode.

14. The method of claim 11, wherein the species sensing electrode portion comprises oxide powders, doped oxide powders, binary oxide materials, ternary oxide materials, vanadium oxides, $V_2O_5$, $WO_3$, $MoO_3$, $BiVO_4$, $BiTaO_4$, $LiVO_3$, $NaVO_3$, $Na_3VO_4$, $KVO_3$, $K_3VO_4$, $Cs_3VO_4$, $MgV_2O_6$, $Mg_2V_2O_7$, $Mg_2V_6O_{17}$, $Mg_5V_4O_{13}$, $Mg_3V_2O_8$, $CaV_2O_6$, $Ca_3V_2O_8$, $Sr_2V_2O_6$, $Sr_2V_2O_7$, $Sr_3V_2O_8$, $CuV_2O_6$, $Ni_3V_2O_8$, $NiV_2O_6$, $CdV_2O_6$, $Cd_2V_2O_7$, $Cd_3V_2O_8$, $CrVO_4$, $Co_3V_2O_8$, $Pb_3V_2O_7$, $CuV_2O_6$, $Cu_5V_2O_{10}$, $AgV_7O_8$, $FeVO_4$, $CeVO_4$, $MnVO_3$, $Mn_2V_2O_7$, $Zn_4V_2O_9$, $Zn_3V_2O_8$, $Zn_2V_2O_7$, $ZnV_2O_6$, $TiVO_4$, $GdVO_4$, $LuVO_4$, $ErVO_4$, $DyVO_4$, $HoVO_4$, $YVO_4$, $TmVO_4$, $YbVO_4$, $TbVO_4$, $SmVO_4$, $NdVO_4$, $AlVO_4$, $TeVO_4$, $SbVO_4$, or mixtures thereof.

15. The method of claim 14, wherein the species sensing electrode portion is doped with a material selected from the group consisting of Ce, Pb, Ag, Mn, Mo, W, Ca, Li, Na, K, Cs, Zr, Ge, Sb, Mg, Sr, Sc, Ti, Nb, Fe, Co, Ni, Cu, Rh, Pd, Ga, In, and Sn, and mixtures and combinations thereof.

16. The method of claim 11, wherein the species sensing electrode portion comprises an additive for creating or enhancing open porosity in the species selective sensing electrode.

17. The method of claim 11, wherein the species sensing electrode portion comprises an additive for creating or enhancing open porosity in the species selective sensing electrode selected from the group consisting of graphite, carbons, open porous glass powder, silica glass powder, regular glass powder, alkali barium borosiliate, and mixtures and combinations thereof.

18. The method of claim 11, wherein the non-active electrode lead portion comprises an alumina additive and optionally further comprises a material selected from the group consisting of platinum, palladium, osmium, rhodium, iridium, gold, ruthenium zirconium, yttrium, cerium, calcium, aluminum, zinc, lanthanum, strontium, cobalt, perovskite, silicon, oxides, mixtures, alloys, cermets, and mixtures and combinations comprising at least one of the foregoing.

19. The method of claim 11, wherein the opening pattern comprises a circular opening, a plurality of circular openings, a rectangular opening, a plurality of rectangular openings, a generally rectangular rounded end opening, a plurality of generally rectangular rounded end openings, or a combination thereof.

20. The method of claim 11, further comprising:
disposing a protective coating layer over the species sensing electrode portion of the species selective electrode.

21. An exhaust gas treatment system comprising:
a sensor comprising a species selective electrode and a reference electrode having an electrolyte layer disposed therebetween; a reference gas channel in fluid communication with the reference electrode; a heater disposed in thermal communication with the sensor; a temperature sensor disposed in communication with the heater for maintaining the sensor at a desired operating temperature; wherein the species selective electrode is disposed on a first side of an insulating layer separating the species selective electrode from the electrolyte layer, the insulating layer having a first substantially solid area and a second area having an opening pattern extending through the insulating layer; the species selective electrode comprising a species sensing electrode portion comprising a first material disposed on the opening pattern of the insulating layer to extend inside at least one opening of the opening pattern so as to contact the electrolyte layer through the opening pattern and a non-active electrode lead portion comprising a second material that is different from the first material, the first material being deposited on top of the second material over the second area, so that the non-active electrode lead portion is in electrical communication with the species sensing electrode portion, said non-active electrode material disposed over the first substantially solid area and the second area so as to substantially surround the periphery of at least one opening in the opening pattern while being sufficiently spaced from the periphery of each opening so as to be free from contact with the electrolyte layer;
the species selective sensing element being disposed downstream of an exhaust catalyst for sensing a concentration of reductant in a catalyst treated exhaust gas;
a controller in communication the species selective sensing element, an engine, and a reductant supply, for controlling the amount of reductant delivered to the exhaust gas exiting the catalyst.

22. The system of claim 21, wherein the species selective electrode is an ammonia selective electrode.

23. The system of claim 21, wherein the exhaust catalyst is a selective catalyst reactor or a urea based selective catalyst reactor.

24. The system of claim 21, wherein the reductant supply is a nitrogen-containing reductant, ammonia, or ammonia prepared from urea.

25. The system of claim 21, wherein the exhaust gas comprises a diesel engine exhaust gas.

26. The sensor of claim 1, wherein the non-active electrode lead portion is disposed over the first substantially solid-area and the second area so as to entirely surround the periphery of at least one opening in the opening pattern.

27. A sensor comprising:

a species selective electrode and an electrolyte layer;

wherein the species selective electrode is disposed on a first side of an insulating layer separating the species selective electrode from the electrolyte, the insulating layer having a first substantially solid area and a second area having an opening extending through the insulating layer;

the species selective electrode comprising a species sensing electrode portion comprising a first material disposed on the insulating layer to extend inside the opening so as to contact the electrolyte layer through the opening, and a non-active electrode lead portion comprising a second material that is different from the first material, the first material being deposited on top of the second material over the second area so that the non-active electrode lead portion is in electrical communication with the species sensing electrode portion, said non-active electrode lead portion disposed over the first substantially solid area and the second area so as to substantially surround the periphery of the opening while being sufficiently spaced from the periphery of the opening so as to be free from contact with the electrolyte layer.

* * * * *